United States Patent [19]

Miller et al.

[11] Patent Number: 5,656,571

[45] Date of Patent: Aug. 12, 1997

[54] POLYOLEFINIC ADJUVANTS

[75] Inventors: Deborah L. Miller; John C. Miller, both of Hawthorn Woods, Ill.

[73] Assignee: Deerpoint Industries, Inc., Hawtorn Woods, Ill.

[21] Appl. No.: 416,617

[22] Filed: Apr. 5, 1995

[51] Int. Cl.$^6$ .................................................. A01N 25/30
[52] U.S. Cl. ........................................ 504/116; 514/937
[58] Field of Search ........................ 585/2, 3, 4, 5, 585/12; 514/937; 427/4; 47/DIG. 11; 43/114; 504/116; 71/DIG. 1

[56] References Cited

U.S. PATENT DOCUMENTS

| | | | |
|---|---|---|---|
| 4,156,321 | 5/1979 | Capizzi et al. | 43/114 |
| 4,397,681 | 8/1983 | Boehme | 71/106 |
| 5,256,419 | 10/1993 | Roe et al. | 424/407 |
| 5,300,255 | 4/1994 | Campbell et al. | 252/351 |

*Primary Examiner*—S. Mark Clardy
*Attorney, Agent, or Firm*—John G. Premo

[57] ABSTRACT

An aqueous polyolefinic emulsion for a biocide composition including an active material selected from the group consisting of insecticides, herbicides, fungicides and rodenticides. Alteratively, the composition can include an active material such as a nutrient or plant growth regulator and the polyolefin can be present in other suitable media to provide, in any embodiment, improved retention/sticker properties.

5 Claims, 7 Drawing Sheets

POLYOLEFINIC ADJUVANTS

BACKGROUND OF THE INVENTION

This invention relates generally to polyolefinic adjuvants and, more particularly, to polyolefinic compositions, solutions and emulsions for enhancing the efficacy of agricultural and horticultural biocides and nutrients or, alternatively, for direct use in the non-toxic extermination of insects.

The effectiveness of any topical agricultural or horticultural treatment depends primarily upon two factors: (1) The retention of the treatment on the plant surface for a time sufficient to achieve the desired result; and (2) coverage of the treatment to provide uniform benefit over the entire plant surface. In the parlance of the industry, a "sticker" is a material that increases the retention of sprays or dust deposits on plants by resisting various weather factors. A sticker is further defined as a substance which increases the firmness of attachment of finely-divided solids or other water-soluble or -insoluble materials to a solid surface, and which may be measured in terms of resistance to time, wind, water, mechanical or chemical action. Typically, stickers are substances such as latex or other adhesives that improve attachment of an active ingredient to sprayed surfaces. In the pesticidal context, stickers protect the active pesticide ingredient from wash-off due to rainfall, heavy dew or irrigation, and help prevent pesticide loss from wind or leaf abrasion.

Likewise, the industry defines a "spreader" as a substance which increases the area that a given volume of liquid will cover. Spreaders are also known as film extenders, wetting agents or surfactants. Notwithstanding the difference in terminology, all such substances reduce the surface tension of spray droplets, increase surface wetting and enhance coverage. Using terminology most often associated with surfactants, use of an anionic spreader on a plant increases the resistance of an active material to removal by rain, dew or irrigation. Anionics also prevent the active ingredient from being readily absorbed through plant cuticles, and such materials are, therefore, used when the effectiveness of the active material depends upon it remaining on the outer surface of the plant. Alternatively, non-ionic spreaders can be used to increase the transport of an active material through plant cuticles and are, therefore, recommended for use with systemic herbicides, nutrients and the like.

As mentioned above, a sticker/spreader combination is used frequently in conjunction or as an adjuvant with various active materials, including biocides, nutrients, plant growth regulators, repellents and the like, to spread the active material more evenly over a plant surface and, if not to promote absorption, to keep it there for a longer period of time. The search for an efficient, effective sticker/spreader meeting these basic requirements has been an on-going concern in the art. Various approaches and chemical systems have been used with certain success, but each has limited utility due to specific, well-defined problems, most of which are related to retention deficiencies and/or incompatibility with the active material or solutions thereof.

Polyvinylpyrrolidones have been used extensively, but are observed to behave more as an encapsulation agent than a sticker. These materials tend to dissolve only very slowly in water and the cost is prohibitive. The various polymenthenes and/or pinches provide reasonable sticking properties, but are difficult to emulsify. Such materials are relatively expensive and tend to be unstable over time, providing an inadequate shelf life under most storage conditions.

Polyethylenes are, perhaps, the most widely used sticker materials, but are—as with the polymenthenes—costly and difficult to emulsify. Performance is also problematic in that the films formed tend to wash off. Polymethylacrylates have also been used, but with limited success. These resins are highly insoluble and form a coating incompatible with many tank mixes. Various surfactants are also used, alone, and promoted as sticker/spreaders. However, as discussed above, without a sticker component, they do not afford to retain the treatment or active material on the plant surface for a sufficient time.

In summary, a considerable number of drawbacks and problems exist in the art relating to stickers and sticker/spreaders. There is a need for an improved sticker and/or sticker/spreader composition to more fully take advantage of the benefits available through use of various biocides, nutrients, repellents and the like.

OBJECTS OF THE INVENTION

It is an object of this invention to provide a polymeric system for use as a retention agent or a retention/surface active composition, either alone or in conjunction with an active material/ingredient, overcoming the problems and deficiencies of the prior art.

It is also an object of this invention to provide a polyolefin for use, included but not limited to, as a sticker composition or in a sticker/spreader combination—with an active material/ingredient or as an adjuvant—or for the non-toxic extermination of insects.

Another object of the present invention is to provide for an olefinic homo- or co-polymer, for use as contemplated herein, which can be used with comparable results either neat, dissolved in a suitable organic solvent, as such a solution emulsified in water, or as an aqueous emulsion without prior dissolution in an organic solvent, whereby when applied to a subject surface shows improved resistance to environmental factors.

Another object of the present invention is to provide a polyolefinic system which is readily emulsified in water, with a variety of suitable surfactants, but does not re-emulsify after application.

Another object of the present invention is to provide a polymeric system, achieving these and other objects discernible to those skilled in the art, which has, essentially, the chemical structure, function, and morphology of a polyolefin, and meets a definition of a polyolefin, notwithstanding the method or process by which it is prepared.

Another object of the present invention is to provide a polymeric system for use as a retention agent or a retention/surface active composition, which can be used with comparable effect over a wide range of molecular weights by modifications in formulation.

Another object of the present invention is to present a polyolefinic system for use, including but not limited to, as a sticker composition or in a sticker/spreader combination—with or without an active material/ingredient or as an adjuvant—which can be designed at the molecular level to provide, through known manufacturing and process techniques and/or reactions, specific structural and performance features.

Another object of the present invention is to provide biocidic, plant growth, nutrient, and defoliant compositions, among others, which are distributable more evenly over a subject surface and retained thereon for a longer period of time.

Another object of the present invention is to provide a polymeric system for use as a retention agent or a retention/ surface active composition which permits improved, more efficient and economical methods of application.

Other objects, features and advantages of the present invention can be derived from the following description of the invention, including the preferred embodiments thereof, taken in conjunction with the accompanying examples and figures.

SUMMARY OF THE INVENTION

This invention is an effective, efficient sticker composition and/or sticker/spreader adjuvant with active materials in the agricultural and horticultural industry. The invention overcomes well-known problems and deficiencies, including those described above.

An important aspect of this invention is the improved sticking function available to the biocidic or like composition through incorporation of a polyolefin. Such resins, whether used alone or in conjunction with a spreader component, can be used in quantities approximating half that required with stickers/spreaders of the prior art to achieve comparable or improved results. When used with spreader component, the polyolefin material forms a stable aqueous emulsion infinitely dilutable in water, rendering it suitable for spray delivery. Alteratively, the polyolefins dissolve readily in various organic solvents, for use directly or as aqueous emulsions. Low molecular weight embodiments can be used neat.

In part, the present invention is a biocidic composition, including (1) an active material or component selected from the group consisting of insecticides, herbicides, fungicides and rodenticides; and (2) an aqueous polyolefin emulsion. In preferred embodiments, the polyolefin is selected from the group consisting of butylene homo- and co-polymers. In highly preferred embodiments, the polyolefin is a co-polymer of isobutylene and butylene monomers. The co-polymer has a molecular weight of about 300–30,000; likewise, in highly preferred embodiments, the molecular weight is about 900–3,000. In alternative embodiments, the butylene co-polymer includes co-monomers selected from the group consisting of isobutylene, styrene, butadiene, isoprene and combinations thereof.

In part, the present invention is an adjuvant composition for enhancing the effectiveness of an active material or component, wherein the composition includes a surfactant and an aqueous polymer emulsion, the polymer consisting essentially of a methyl-substituted polyolefin. In preferred embodiments, the polyolefin is selected from the group consisting of isobutylene homo- and co-polymers having a molecular weight of about 300–30,000. When present as an isobutylene co-polymer, the polyolefin includes co-monomers selected from the group consisting of butylene, styrene, butadiene, isoprene and combinations thereof. In highly preferred embodiments, the polyolefin is a co-polymer of isobutylene and butylene. Whereas the co-polymer can have a molecular weight of about 300–30,000, preferred embodiments have a molecular weight of about 900–3,000.

In part, the present invention includes vegetative material having applied thereto a biocidic composition as described above. In preferred embodiments, the composition further includes a surfactant to extend the composition evenly over the surface of the vegetative material. As described above, the polyolefin is a co-polymer including isobutylene and butylene monomers, having a molecular weight of about 300–30,000. In highly preferred embodiments, the co-polymer has a molecular weight of about 900–3,000.

In part, the present invention is a sticker composition for retaining active materials on a vegetative surface, including an alkyl-substituted polyolefin having a molecular weight of about 300–30,000. The polyolefin is in a liquid medium and forms a water-insoluble deposit on the vegetative surface upon drying. In preferred embodiments, the polyolefin is a co-polymer including isobutylene and butylene monomers. The liquid medium is an organic solvent within which the polyolefin is dissolved. Alternatively, the liquid medium is water and the composition further includes a surfactant in an amount sufficient to emulsify the polyolefin.

In part, the present invention is a method for exterminating insects positioned on a plant or other surface, the method including (1) preparing an alkyl-substituted polyolefin material, (2) applying the polyolefin material to the plant surface, and (3) entrapping the insects with the polyolefin, whereby the insects are asphyxiated. In preferred embodiments, the polyolefin is selected from the group consisting of isobutylene homo- and co-polymers. In highly preferred embodiments, the polyolefin is a co-polymer including isobutylene and butylene monomers, with the co-polymer having a molecular weight of about 300–3,000. The polyolefin can be applied to the plant surface with a liquid medium selected from water or an organic solvent within which the polyolefin is soluble. Where the medium is water, the polyolefin is emulsified with a surfactant.

As discussed above, a sticker of the present invention used alone or in combination with a spreader component enhances the effect achieved through use of an active material such as a herbicide, pesticide, fungicide, rodenticide, nutrient, plant growth regulator, pheromone, defoliant and the like. The inventive polymeric compositions, sticker/spreader combinations, and adjuvants of the present invention are effective in lower dosages than otherwise available through the prior art, are compatible with active materials with respect to handling and application techniques, dissolve or emulsify readily in an appropriate organic or aqueous solvent, and are stable over long storage periods. When used alone or in combination with a spreader component, the polyolefins of the present invention enhance the retention of an active material on a plant or other surface by increasing the resistance to removal by wind, water, and/or mechanical action. When used in combination with the inventive polyolefins and in accordance with this invention, various spreader components ensure adequate coverage of the polyolefin in a homogeneous manner over the entire surface area. In such a way, the sticker and spreader components of the present invention act synergistically to improve the performance and cost-efficiency of the active material. Savings are further realized through lower quantities and/or concentrations of the sticker and/or sticker/spreader combination required to achieve comparable or better results.

The stickers of the present invention include olefinic homo- and co-polymers. As mentioned above, preferred embodiments of this invention include alkyl-substituted polyolefins—in particular, methyl and like substituted polyolefins of the type available through incorporation of isobutene, isobutylene or butene monomers. Various polyolefinic and alkyl-substituted polyalkene stickers, all in accordance with this invention, can be designed to meet specific performance requirements through selection of specific monomeric starting materials, subsequent synthetic manipulation of the polymeric chain, or choice of reaction and process conditions. Consistent with the present invention, the polyolefins and/or alkyl-substituted polyalkenes described herein include those commercial products which are essentially such polymerized olefins and/or related alkanes, notwithstanding the presence of one or more unsaturated centers/moieties inconsequential to their function as stickers and/or adjuvants or as artifacts of the particular synthetic procedure employed, whether or not subsequently reduced to the polyolefin or alkane.

The molecular weight of the inventive polymer is limited only by application and use conditions. Typically, but without limiting the present invention, a polyolefin—such as that described above and having a molecular weight of about 300—can be used neat or with emulsification or dissolution in an appropriate solvent. At higher molecular weights or in combination with more carbon branching off the polymeric backbone, an appropriate liquid medium is required to ensure efficient sticker application on the subject surface. The molecular weight of the inventive polyolefins can be determined by methods well-known to those skilled in the art, in particular by the AM-S 320.06 test method. The molecular weight of any given polyolefin is theoretically unlimited and the higher molecular weight embodiments can be accessed through straight-forward modifications of synthetic procedures also well-known to those skilled in the art and made aware of this invention. At molecular weights higher than 30,000, solubility of the olefinic sticker is problematic and, in the emulsion context, the amount of surfactant required is cost-prohibitive. As mentioned above, in preferred embodiments whether used alone or in combination with a spreader component, the molecular weight of the polyolefin is about 900–3,000. Polyolefinic stickers having a molecular weight within this range can be easily incorporated into a variety of use applications.

In highly preferred embodiments, the polyolefinic sticker component is a polyisobutylene/butene co-polymer, with a molecular weight of about 1300 or, alternatively, a polyisobutylene-butene co-polymer, having a molecular weight of about 2500. Both embodiments, among others, are commercially available from Deerpoint Indushies, Inc. of Hawthorn Woods, Ill. under the DPI S100 and DPI S200 trademarks, respectively. Other embodiments of this invention, in particular the sticker component thereof, are available from other commercial sources well-known to those skilled in the art who are made aware of this invention.

Although the sticker component of the present invention can be used neat, as when employed as a non-toxic insecticide or in conjunction with an active material, numerous applications require dissolution in a suitable organic solvent or emulsification in water. With respect to the latter and given the insoluble nature of these materials, emulsification is accomplished through use of a suitable surfactant, which further acts as a spreader or film extender for uniform application on the subject surface. Depending upon the desired use and effect of the active material, the surfactant may be either ionic or non-ionic. In preferred embodiments, such as with the DPI S100 and DPI S200 commercial products, as described above, one of many available sulfonate surfactants is employed, the choice of which depends, in part, upon cost and compatibility with the active material or the liquid medium within which it is present.

The following non-limiting examples illustrate these and other features of the invention.

EXAMPLES OF THE INVENTION

Figure 1A:
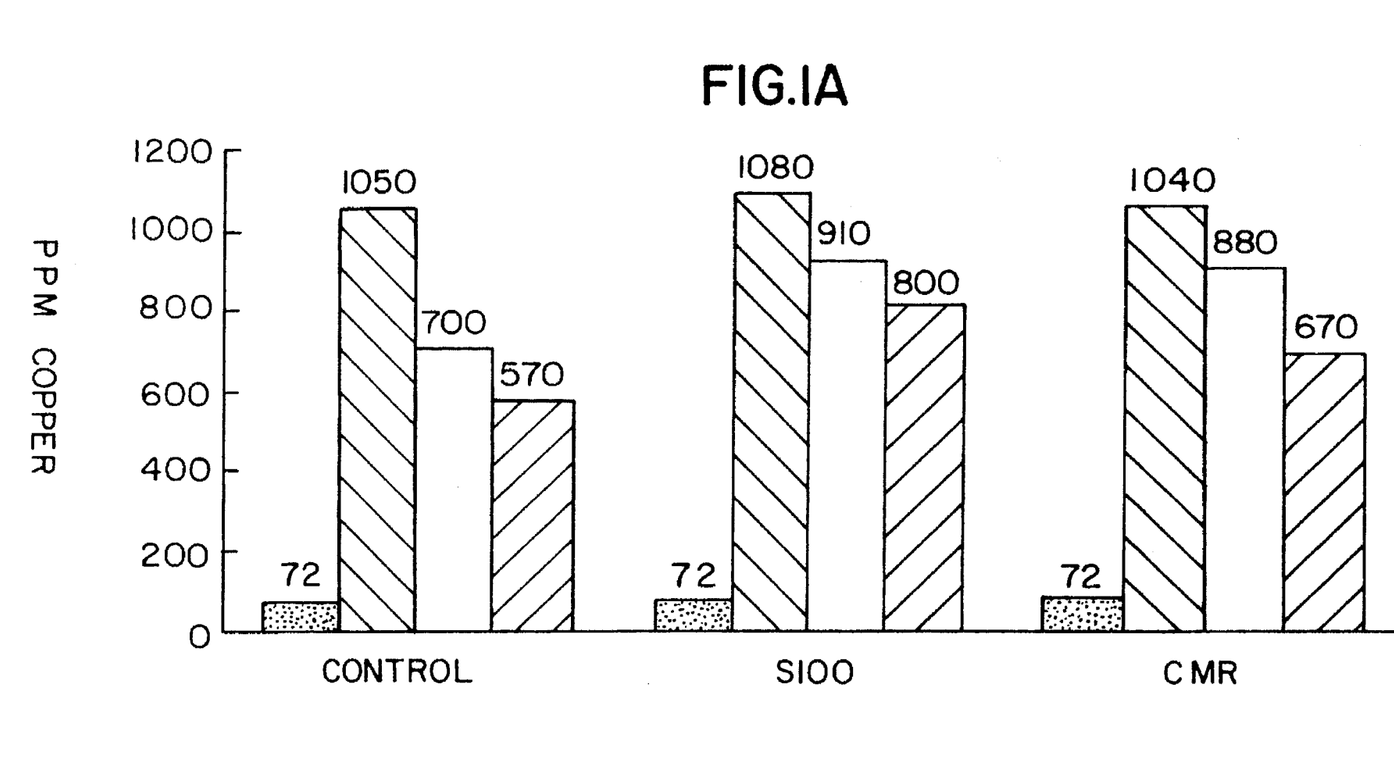
FIG. 1A graphically illustrates, by comparison, the levels and/or retention of Cu on ornamental tree leaves sprayed with the fungicide NORDOX, alone, with a prior art product, and with an olefinic copolymer (DPI S100) in accordance with this invention—before spraying (solid), post-spray (///), at two weeks (open), and at four weeks (\\\)
Figure 1B:
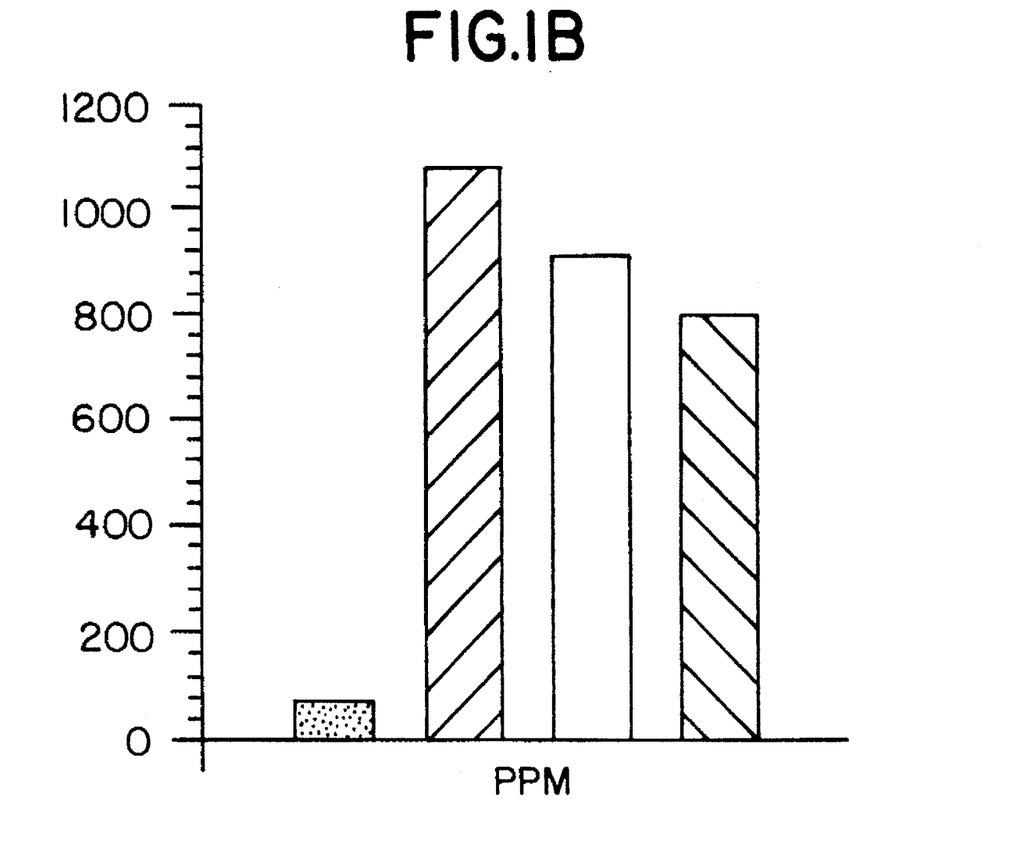
FIG. 1B graphically extends the comparison of FIG. 1A to include another olefinic copolymer (DPI S200) of the present invention—before spraying (solid), post-spray (white dots), at two weeks (black dots), and at four weeks (xxx)
Figure 2A:
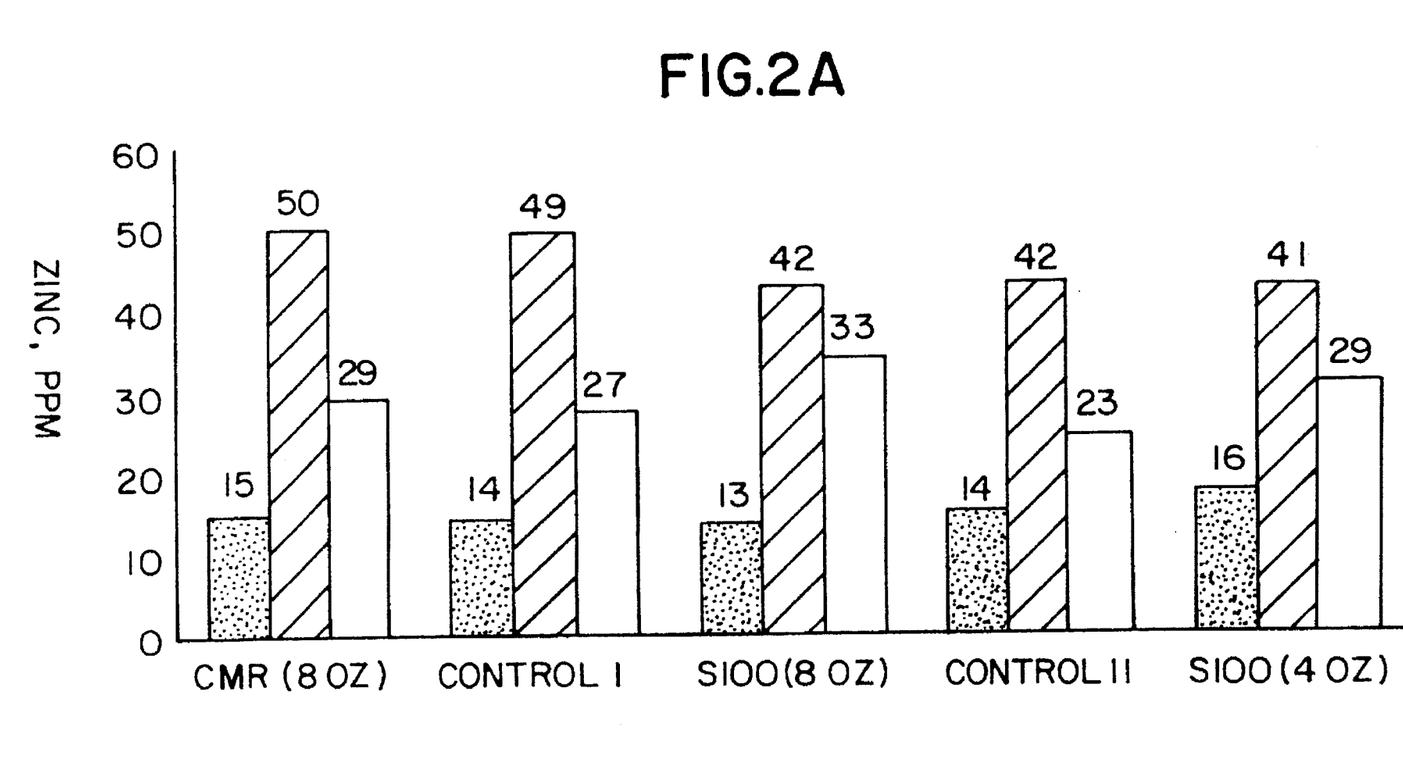
FIG. 2A graphically illustrates, by comparison, the levels and/or retention of Zn on cherry tree leaves sprayed with a standard nutrient/pesticide treatment, alone, with a prior art product, and with different concentrations of an olefinic copolymer (DPI S100) in accordance with this invention—before spraying (solid), at one month (///), and at three months (xxx)
Figure 2B:
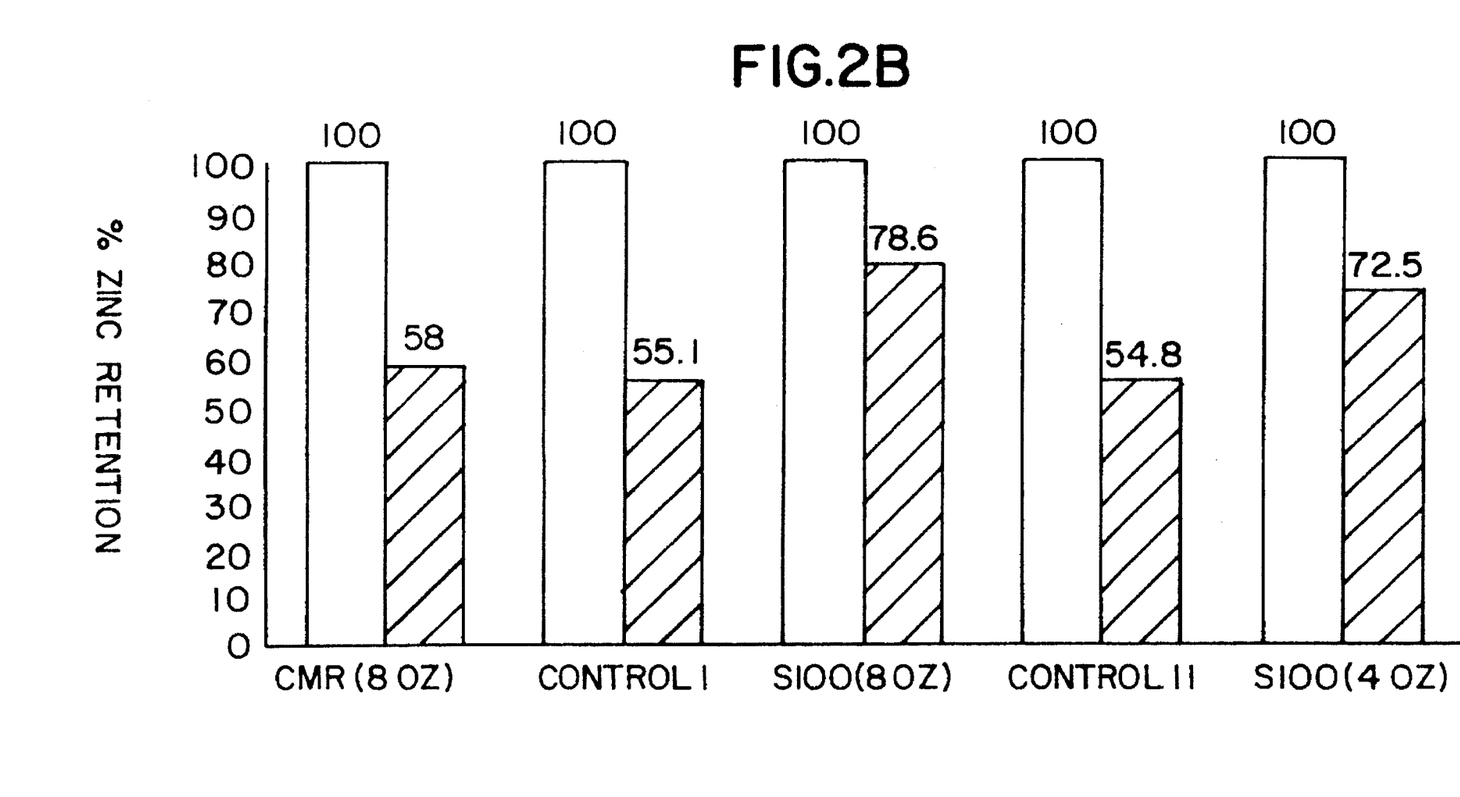
FIG. 2B amplifies the comparison of FIG. 2A by normalizing the one-month Zn level (solid) and expressing the three-month retention levels as a percentage thereof (////)

A specific use and/or application of the sticker/adjuvant compositions of this invention will, in part, determine the particular embodiment or formulation employed. For example, ground application can entail use of various diluted full-volume or concentrated sprays. With respect to the former, 8–16 fluid ounces of the composition, solution, or emulsion, more or less depending upon the coverage and effect desired, per 100 gallons of water or active material/agent is effective. For concentrated sprays, the same volumes can be used, without dilution, as required to wet foliage. Aerial applications typically require lower volumes—normal use rates are about 4–8 fluid ounces per acre, but may meet or exceed 16 fluid ounces per acre. If applied with a spray, it is advantageous to add the inventive composition, solution, or emulsion as the spray tank is filled—with agitation, if possible. Pre-mixing is not required before addition to the spray tank because the polyolefins of this invention are stable during storage, whether neat, in solution or as part of an aqueous emulsion. The quantity and/or concentration will also vary with water hardness, equipment characteristics, temperature, and type (surface characteristics) of foliage to be treated.

Example 1

Two polyolefin compositions of this invention were compared with a widely-used standard of prior art, a mixture of alkylphenoxy polyethoxy ethanols in cottonseed oil available under the CMR trade designation, to determine the retention/longevity of NORDOX, the trade name of a common, commercial copper oxide fungicide. The labeled, advised rate of NORDOX with or without the respective adjuvant, as shown below, was applied to four separate ornamental trees, using a hand-held carbon dioxide, backpack-type sprayer with two-foot booms and dual nozzles. NORDOX was used, alone, as a control. The DPI S100 (FIG. 1A) and DPI S200 (FIG. 1B) sticker/spreaders of this invention were used at a concentration of 8 fluid ounces per 100 gallons of NORDOX. The CMR product was used at a concentration of 32 fluid ounces per 100 gallons of NORDOX.

A random sampling of leaves were prepped according to standard procedures and analyzed by atomic absorption spectroscopy to determine a base Cu level (72 ppm). Immediately after application, leaves were randomly pulled, prepped and analyzed to determine the increase in Cu levels. The sampling and analysis was repeated at two weeks, then at four weeks to compare NORDOX retention. The results, summarized in FIGS. 1A and 1B, show conclusively that the polyolefins of this invention—at concentrations four times lower than the prior art—retain more active material/ingredient for longer periods of time. In particular, using the DPI S100 sticker/spreader, Cu retention was observed after four weeks to be 20% greater than the retention available through use of the prior art compositions.

Example 2

The results of Example 1 were extended to nutrient retention, with similar effect. The DPI S100 polyolefin sticker/spreader, in accordance with this invention, was compared with the CMR standard of the prior art. The compositions were tested in conjunction with a cherry orchard treatment comprising the zinc salt of ethylenediaminetetraacetic acid (nutrient), DIAZINON (insecticide) and CENIPHOS (phosphoric acid, to adjust pH and as a nutrient source). In all treatments tested, both the initial zinc nutrient and DIAZINON concentrations were 1 pound per 100 gallons (2.5 pounds per acre over the 10-acre cherry orchard test plot), and the initial CENIPHOS concentration was 1 gallon per 100 gallons.

The ten-acre plot was divided into five two-acre sub-plots, with control sub-plots separating each of three test sub-plots. The cherry trees in each control sub-plot were sprayed with the nutrient and insecticide treatment at the concentrations described above. Trees of the first test plot were sprayed with a CMR-modified (8 fluid ounces per 100 gallons) nutrient/insecticide treatment. The second test plot was sprayed with a DPI S100-modified (8 fluid ounces per 100 gallons) nutrient/insecticide treatment. Trees of the third test plot were sprayed with a DPI S100-modified (4 fluid ounces per 100 gallons) nutrient/insecticide treatment.

A random sampling of leaves were prepped according to standard procedures and analyzed by atomic absorption spectroscopy to determine a base Zn level (13–16 ppm). Approximately one month after application, 100 cherry leaves were selected from each test plot, the sampling technique involving leaves from every other tree in the plot and from alternate sides of each row. In a similar fashion, 100 cherry leaves were sampled at approximately 3 months. After each sampling, the leaves were prepped and analyzed to determine Zn levels and compare nutrient retention.

The raw data of FIG. 2A and normalized data of FIG. 2B show that the sticker/spreaders of this invention enhance effectiveness of treatment by increasing longevity of the active material/ingredient on the leaf. As compared to treatment with the CMR standard, the same concentration of the DPI S 100 sticker/spreader of this invention affords, after three months, a 23% increase in Zn retention. Use of the DPI S 100 composition at a concentration one-half that of the CMR standard provides a 14.5% increase in Zn retention after three months. Because total Zn content was measured without distinction as to that present on the leaf surface and that transported into the leaf, a reasonable inference is that any increase in detectable levels is a reflection of longer surface retention in any event.

The following examples show the polyolefins of the present invention to be efficacious as insecticides. Their inert nature and low toxicity suggest that they are non-toxic, but act, rather, by physical means to hold, entrap, and/or asphyxiate insect pests, as illustrated below. Various principles and concepts concerning the use, behavior, and effect of non-toxic insecticides are described in U.S. Pat. No. 5,089,266, incorporated herein in its entirety.

Example 3a

Six spiders were placed in a glass container having an internal volume of approximately 55 cubic inches. The spiders were observed visually for approximately 15 minutes to establish an activity baseline. A 0.5% aqueous solution of DPI S100 sticker/spreader composition was prepared for spray dispersion. Approximately 0.4 grams of the DPI S100 solution (2.0 mg polyolefin) was sprayed into the container and left open to the atmosphere. After 62 minutes all activity ceased, and the spiders were observed to be exterminated.

Example 3b

Six spiders were placed in a glass container having an internal volume of approximately 55 cubic inches. The spiders were observed visually for approximately 15 minutes to establish an activity baseline. A 0.5% aqueous solution of DPI S100 sticker/spreader composition was prepared for spray dispersion. Approximately 0.5 grams of the DPI S100 solution (2.5 mg polyolefin) was sprayed into the container and left open to the atmosphere. After 73 minutes, 100% extermination was observed. Examples 3a and 3b (both pre- and post-application) were video recorded.

Example 4a

A pony-tail palm plant uniformly infested with spider mites was segmented into two approximately equal sections through use of a plastic wrap over one-half of the infested plant. The mites exhibited normal movement and activity. The number of mites in each section was visually estimated to exceed 200. With one section isolated in this manner, the plant was sprayed with 5–6 grams of a 1.0% aqueous solution of DPI S100 sticker/spreader composition. Immediately after spraying, the plastic wrap was removed, thereby providing a control section. Through visual observation of the section sprayed with the inventive composition, 100% of the spider mites were exterminated within 30 seconds. The control section was observed to have a 0% extermination ratio.

Example 4b

An isolated segment of a common palm plant was observed to be infested with approximately 40 spider mites, exhibiting normal movement and activity. A 0.5% aqueous solution of DPI S100 sticker/spreader was prepared for spray dispersion. The affected area was sprayed with 0.8 grams (4.0 mg polyolefin) of the inventive solution, and 100% of the spider mites were immediately exterminated, as confirmed by visual observation. Example 4b (both pre- and post-application, for one hour each) was video recorded.

The following examples illustrate use of the inventive polyolefin compositions to control the release of inactive material. As described above, these compositions can be used as aqueous emulsions, but can also be employed neat or diluted with a suitable organic solvent-depending upon the molecular weight. By way of illustration, methyl bromide was chosen as the active material. Methyl bromide is a volatile gas at room temperature and used in the agricultural industry as a soil fumigant/pesticide. Under typical field procedures, the methyl bromide is injected into the soil as a gas, while the soil is simultaneously covered with an appropriately impermeable plastic tarp or plastic film to ensure sufficient contact time and pesticidal activity. Treating large fields in this manner is very costly and time consuming, requiring sophisticated equipment. The following examples show the present invention to afford distinct advantages over the prior art.

Example 5

Figure 3:
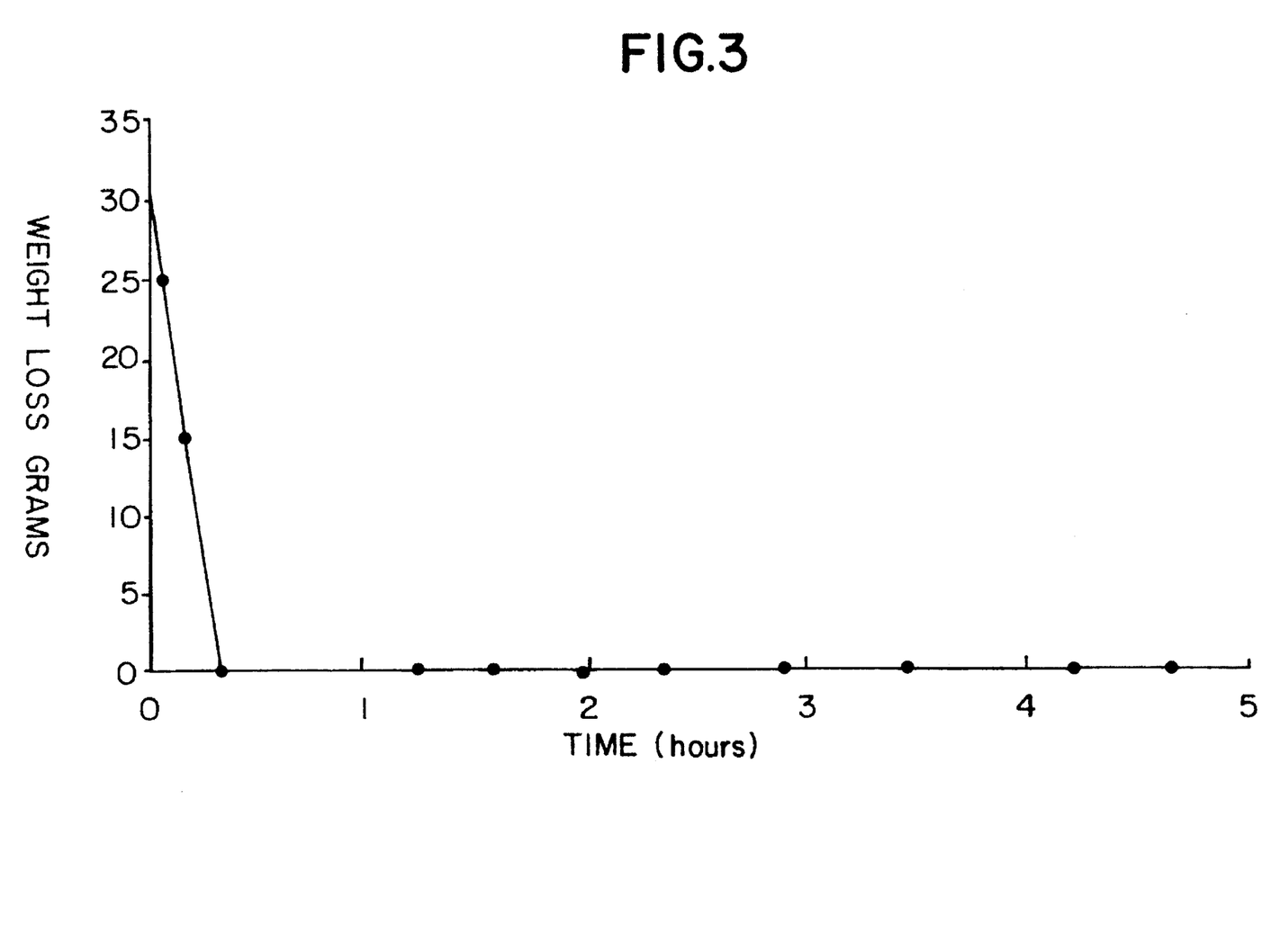
FIG. 3 plots the loss of methyl bromide over time upon exposure to the open atmosphere.

As a control, 30 grams of methyl bromide was placed in a sealed 8 inch square glass container, placed on balance, then exposed to the atmosphere at room temperature. FIG. 3 shows the weight loss of methyl bromide observed as a function of time.

Figure 4:
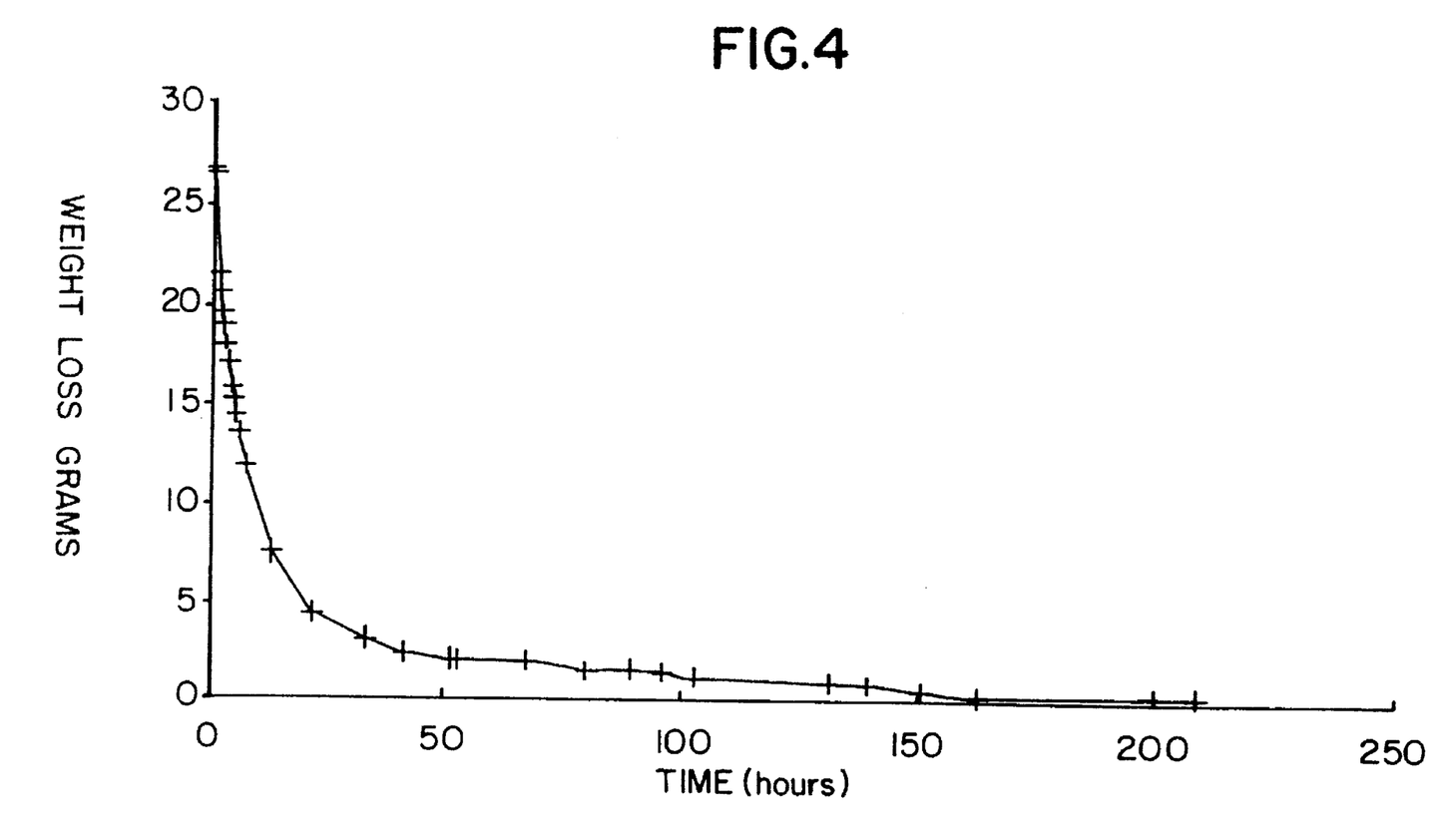
FIG. 4 tracks loss of methyl bromide from a corn oil/polyisobutylene solution, over time.

Approximately 30 grams of methyl bromide was dissolved in 200 grams of a 1:1(w/w) solution of a commercial corn oil and polyisobutylene (MW=1,000). The methyl bromide/polyolefin composition was placed in a sealed eight inch square glass container, place on a balance, and exposed to the atmosphere at room temperature. Inasmuch as neither the oil nor the polyolefin are volatile or reactive, FIG. 4 shows the weight loss of methyl bromide observed as a function of time. With comparison to FIG. 3, it is seen that the inventive polyolefin controls the release of methyl bromide, increasing potential contact time and enhancing its pesticidal activity. After twenty-four hours, an appreciable amount of the active bromide is still available for fumigation.

Example 6

Figure 5:
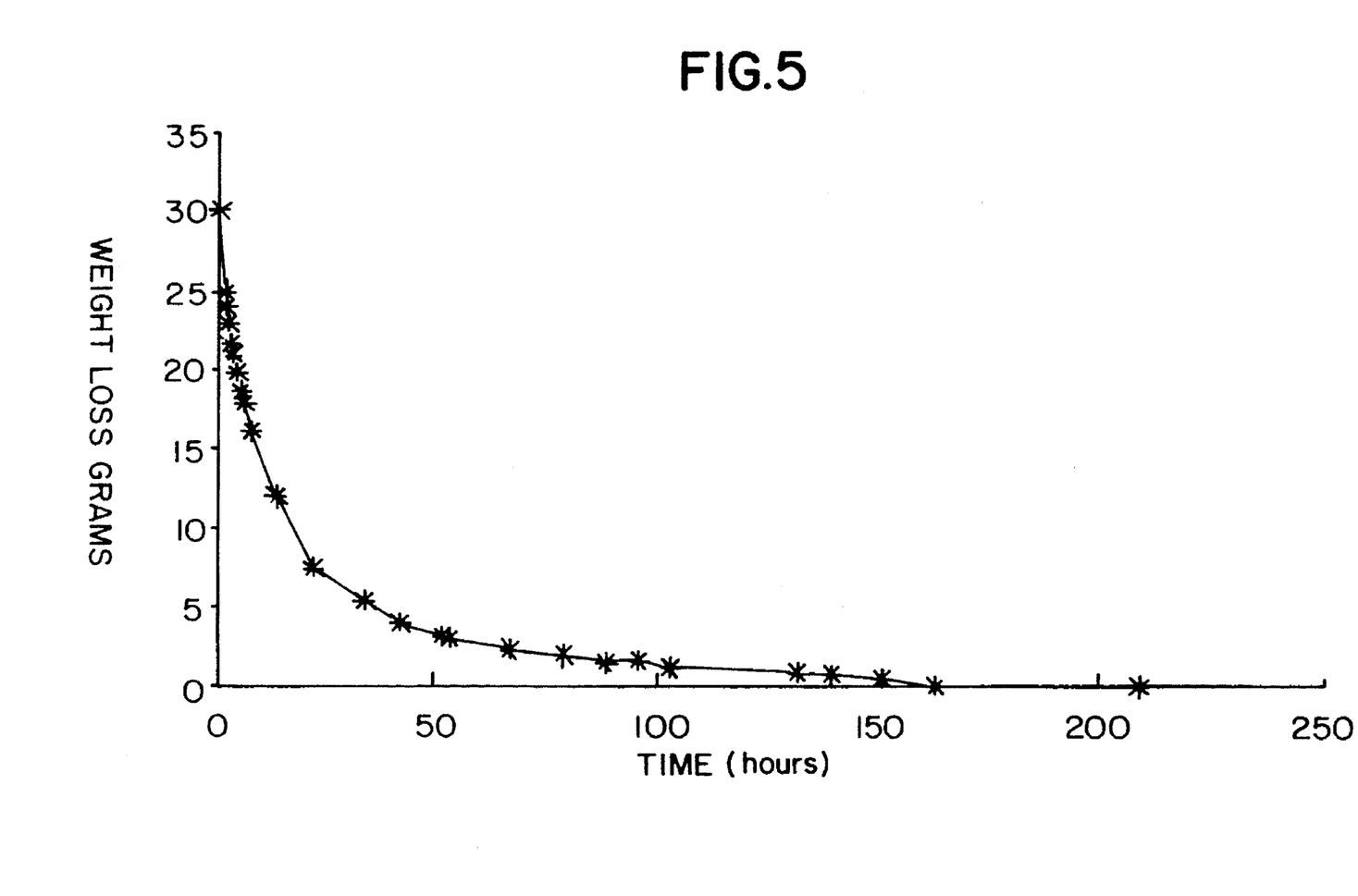
FIG. 5 records the loss of methyl bromide from neat polybutene, over time.

Approximately 30 grams of methyl bromide was dissolved in 200 grams of neat polybutene (MW=1,000). This solution was placed in a sealed eight-inch square glass container, placed on a balance, then exposed to the atmosphere at room temperature. Again, because the oil and polyolefin are non-volatile and non-reactive, FIG. 5 shows the weight loss of methyl bromide observed as a function of time. As shown with he previous example, a significant mount of methyl bromide is available for a longer period of time, thereby promoting its effect as a fumigant/pesticide.

As observed with the previous example, only negligible amounts of methyl bromide remain after 4–5 days. Because prolonged contact with methyl bromide can be detrimental to plant growth and/or the harvestable crop, the depletion observed meets another crucial requirement of soil fumigation.

Example 7

The utility of two sticker/spreader combinations oft he present invention was demonstrated in conjunction with a winter weed treatment and, simultaneously, compared with the CMR product of the prior art. In this example cacodylic acid, a contact herbicide, is the active material. (A commercial preparation of cacodylic acid is available under the MONTAR tradename from Monterey Chemical Company of Monterey, Calif.). Contact herbicides are useful for demonstrating improved longevity and retention, inasmuch as these factors are critical to their effectiveness. As indicated on the manufacturer's label instructions, cacodylic acid—as with other contact herbicides—are most effective when applied under sunny conditions.

Four herbicidal mixtures were prepared, each including the commercial MONTAR product, an aqueous solution of cacodylic acid in sufficient amount to afford 7.44 pounds of the active ingredient per acre. MONTAR was used alone on a 6×100 foot lot populated by a mixture of grass and broadleaf weeds. Test plot No. 1 (6×100 feet) was sprayed with a CMR-modified (16 fluid ounces per 100 gallon tank mix) MONTAR product. Test plot No. 2 (6×100 feet) was sprayed with DPI S100-modified (16 ounces per 100 gallon tank mix) MONTAR product. Test plot No. 3 (6×100 feet) was sprayed with DPI S200-modified (16 fluid ounces per 100 gallon tank mix) MONTAR product. On all test plots, as with the control plot, a backpack type carbon dioxide sprayer with a hand-held wand and a six foot, 4-nozzle spray boom was utilized. It should be understood that the test of this example was initiated under cold, wet weather conditions—less than ideal for contact herbicides.

The efficacy of each MONTAR spray applied was evaluated by the rate of kill, on a scale of 0 to 10, with 0 indicating no weed kill whatsoever and 10 indicating total kill (i.e., bare ground). The control and test plots were observed daily for two weeks, then weekly for three months. The results, with numerical ratings, are summarized below in Table 1.

Table 1.

1. Initial Kill (Weeds Dead or Severely Yellowed at 7 days):

Control plot—2.

CMR Spreader/Sticker—5.

DPI S100 Sticker/Spreader—6. *

DPI S200 Sticker/Spreader—6. *

*The DPI-treated plots showed signs of weed kill earlier than did CMR and Control plots.

2. Final Kill After 2 weeks (Maximum Kill attained with Trial):

Control—3.

CMR Spreader/Sticker—6

DPI S100 Sticker/Spreader—8.

DPI S200 Sticker/Spreader—8.

Longevity of Weed Kill After 3 months:

Two and three months after spraying, plots were re-observed to determine the return of weed growth. The Control plot was indistinguishable from the surrounding, unsprayed filed, without indication that the plot had been sprayed. The CMR treated plot weeds had largely grown back, although faint outlines of the spray area were detectable. The DPI S100 and S200 plots still had very noticeable weed knockdown, with the plots clearly delineated, as compared to the surrounding field, by their lack of weed regrowth.

Control—0.

CMR Spreader/Sticker—1

DPI S100 Sticker/Spreader—6.

DPI S200 Sticker/Sprader—6.

While the principles of this invention have been described in connection with specific embodiments, it should be understood clearly that these descriptions are made only by way of example and are not intended to limit the scope of the invention, in any manner. For example, the techniques, sticker compositions, spreader compositions, sticker/spreader combinations, and active materials available can be employed by those skilled in the art in a fashion analogous to those described herein to treat a wide variety of plants and/or enhance plant growth. While several examples are provided by way of demonstrating the type of plant, active material, sticker, and/or sticker/spreader compositions contemplated by the present invention, other useful combinations are available through well-known formulation techniques and application processes. As such, the present invention can be extended with beneficial results to the retention and dispersion of various protective coatings on numerous fruit and vegetable varieties for protection from excessive heat, cold or sun exposure. For instance, a kaolin/clay composition available under the SNOW trademark from the Wilbur-Ellis Company of Fresno, Calif., can be used in conjunction with the present invention when formulated and applied as described herein. The resulting combination enhances solar reflectance and reduces crop damage, sunburn and sun scald. While the efficacy of the inventive polyolefins has been demonstrated with spiders and spider mites, the present invention also extends to the use thereof for the extermination of other insects predisposed to such non-toxic substances. Other advantages and features of the invention will become apparent from the claims hereinafter, with the scope of the claims determined by the reasonable equivalents, as understood by those skilled in the art.

What is claimed is:

1. A non-foaming adjuvant composition which is combined with and enhances the effectiveness of an active material selected from the group consisting of insecticides, herbicides, fungicides rodenticides nutrients, plant growth regulators, pheromones and defoliants which adjuvant composition prior to being combined with the active material is an emulsion comprising an aqueous phase which contains a surfactant and a polymer consisting essentially of a methyl-substituted polyolefin having a molecular weight of about 300–30,000.

2. The composition as defined in claim 1 wherein said polyolefin is selected from the group consisting of isobutylene homo- and co-polymers.

3. The composition as defined in claim 2 wherein said polyolefin is a co-polymer comprised of isobutylene and butylene monomers.

4. The composition as defined in claim 3 wherein said co-polymer has a molecular weight of about 900–3,000.

5. The composition as defined in claim 2 wherein said polyolefin is an isobutylene co-polymer comprising co-monomers selected from the group consisting of butylene, styrene, butadiene, isoprene and combinations thereof.

* * * * *